(12) United States Patent
Tecotzky et al.

(10) Patent No.: US 6,909,795 B2
(45) Date of Patent: Jun. 21, 2005

(54) COMMUNICATING COMPUTER-AIDED DETECTION RESULTS IN A STANDARDS-BASED MEDICAL IMAGING ENVIRONMENT

(75) Inventors: Raymond H. Tecotzky, Fremont, CA (US); Julian Marshall, Los Altos, CA (US)

(73) Assignee: R2 Technology, Inc., Sunnyvale, CA (US)

( * ) Notice: Subject to any disclaimer, the term of this patent is extended or adjusted under 35 U.S.C. 154(b) by 53 days.

(21) Appl. No.: 10/463,627

(22) Filed: Jun. 16, 2003

(65) Prior Publication Data

US 2004/0252871 A1 Dec. 16, 2004

(51) Int. Cl.[7] .............................. G06K 9/00; G06F 17/60
(52) U.S. Cl. ............................ 382/128; 382/132; 705/2
(58) Field of Search ................................ 382/128–134; 705/2; 600/437; 378/29

(56) References Cited

U.S. PATENT DOCUMENTS

| 5,917,929 A | * | 6/1999 | Marshall et al. ............ 382/128 |
| 2002/0019751 A1 | | 2/2002 | Rothschild et al. | |

FOREIGN PATENT DOCUMENTS

WO    WO 00/33157    6/2000

OTHER PUBLICATIONS

Horii, Steven C., "A Nontechnical Introduction to DICOM," RadioGraphics 1997:1297–1309 (RSNA 1997).
National Electrical Manufacturers Association, *Digital Imaging and Communications in Medicine (DICOM), PS 3.3–2003 Part 3: Information Object Definitions*, (NEMA 2003) at pp. 1–165.
National Electrical Manufacturers Association, *Digital Imaging and Communications in Medicine (DICOM), PS 3.4–2003 Part 4: Service Class Specifications*, (NEMA 2003) at pp. 1–25, 229–236, 299–301.
National Electrical Manufacturers Association, *Digital Imaging and Communications in Medicine (DICOM), PS 3.6–2003 Part 6: Data Dictionary*, (NEMA 2003) at pp. 1–7, 77–85.
National Electrical Manufacturers Association, *Digital Imaging and Communications in Medicine (DICOM), PS 3.16–2003 Part 16: Content Mapping Resource*, (NEMA 2003) at pp. 1–77.
R2 Technology, Inc., "DICOM Conformance Statement M1000–DM, V2.3A" (Feb. 2001).
"Second Look® Analog DICOM Conformance Statement", CADx Systems, Inc., Document# 1111–1004–1, 20–page document, Rev. (Feb. 14, 2003).

* cited by examiner

*Primary Examiner*—Bhavesh M. Mehta
*Assistant Examiner*—Duy M. Dang
(74) *Attorney, Agent, or Firm*—Brian J. Daluto (57) ABSTRACT

A method, system, and method of doing business in a standards-based medical imaging environment is described in relation to the communication of computer-aided detection (CAD) results among devices, with one embodiment relating to the DICOM standard. CAD results are fixably integrated into the pixels of a secondary image derived from a source image, and the secondary image is transferred using a DICOM Secondary Capture Image Information Object Instance (SCI-IOI). The DICOM SCI-IOI is transferred to a viewing workstation, whereby a clinician can open, manipulate, and view the secondary image in a side-by-side comparison with the source image or derivative images thereof. Advantageously, CAD results are communicated to the clinician in a DICOM-conforming manner independent of whether the viewing workstation supports standard DICOM accommodations, such as CAD Structured Report Information Object Instances (CAD SR-IOIs), for the type of CAD results that need to be presented. Optionally, an equipment information entity identifier in a CAD SR-IOI and/or the SCI-IOI can be modified to change or shield the identity of the manufacturer of the CAD processing unit.

26 Claims, 8 Drawing Sheets

COMMUNICATING COMPUTER-AIDED DETECTION RESULTS IN A STANDARDS-BASED MEDICAL IMAGING ENVIRONMENT

FIELD

This patent specification relates to the computer-aided detection of abnormalities in medical images. More particularly, this patent specification relates to communicating and displaying computer-aided detection results in a medical imaging environment that operates, at least in part, according to a standard medical imaging communications protocol such as the DICOM standard.

BACKGROUND

The industrial standards process has generally been recognized as a permissible form of cooperation among otherwise competing enterprises. By promoting operational compatibility and apples-to-apples comparison of products and services, the standards process can lead to enhanced consumer choice, greater competition, and increased technological innovation. However, the possibility exists that a larger enterprise having an established market presence might only selectively activate certain features of an agreed-upon standard in order to obtain an advantage over market entrants or smaller competitors. For example, the larger enterprise might choose to impose certain conditions, such as bundling conditions, on the sale of a key system component before activating the supposedly "standard" features within that key system component. Purchasers of the key system component are thereby "forced" to purchase any complementary system components from that same larger enterprise, much to the detriment of market entrants and smaller competitors who relied on the existence of the agreed-upon standard in developing their own complementary components. At least in part, the present patent specification relates to an instance of this "selective standards activation" scenario that might be found, either presently or prospectively, in the medical imaging industry.

The DICOM standard (Digital Imaging and Communications in Medicine) is defined and maintained by the National Electrical Manufacturers Association, and is directed to providing a common framework for the acquisition, transmission, archiving, retrieval, and presentation of medical images of the human body and related patient data for a variety of imaging modalities and environments. As discussed in Horii, "A Nontechnical Introduction to DICOM," RadioGraphics 1997:1297–1309 (RSNA 1997), the DICOM standard is highly adaptable and continues to grow to accommodate advances in medical imaging technology. According to Horii, the fact that many of the medical imaging equipment manufacturers are global corporations has sparked considerable international interest in DICOM, with both European and Japanese standards organizations adopting substantial portions of DICOM. The DICOM standard is maintained and extended by the DICOM Standards Committee, which is an international, multi-specialty committee.

Currently, the DICOM standard consists of sixteen published parts, PS 3.1-2003 through PS 3.16-2003, describing different aspects of the DICOM standard. By way of example, the first published part is a 20-page document that can be fully cited as "National Electrical Manufacturers Association, Digital Imaging and Communications in Medicine (DICOM), PS 3.1-2003 Part 1: Introduction and Overview, (NEMA 2003)." This document can more briefly be cited as "PS 3.1-2003: Introduction and Overview," "PS 3.1-2003," or, most simply, "PS 3.1," it being understood that the latter is a reference to the current year, a past year, or a group of years according to the context. Among other published parts of the DICOM standard relevant to the present disclosure are the third part, "PS 3.3-2003: Information Object Definitions," the fourth part, "PS 3.4-2003: Service Class Specifications," the sixth part, "PS 3.6-2003: Data Dictionary," and the sixteenth part, "PS 3.16-2003: Content Mapping Resource."

Recent additions to the DICOM standard have been made to accommodate the field of computer-aided diagnosis (CAD) in which specialized computer programs analyze medical images to detect anatomical abnormalities, or lesions, therein. Sometimes used interchangeably with the term computer-aided diagnosis are the terms computer-aided detection, computer-assisted diagnosis, or computer-assisted detection. The outputs of CAD systems, generally referred to herein as CAD results, are sets of information sufficient to communicate the locations of anatomical abnormalities, or lesions, in a medical image, and can also include other information such as the type of lesion, degree of suspiciousness, and the like.

Examples of a mammography CAD system are presented in U.S. Pat. Nos. 5,729,620 and 5,917,929, which are incorporated by reference herein. An example of a chest CAD system is presented in WO02/056240, which is incorporated by reference herein. It is to be appreciated that, although particular references to mammography and chest CAD system are provided infra, the scope of the preferred embodiments includes any of a variety of CAD systems that receive 2D or 3D medical images of a body part and detect, automatically or with manual assistance, anatomical abnormalities therein. Examples include colon CAD systems, bone CAD systems, and other CAD systems.

It is to be further appreciated that although particular reference to x-ray mammography and chest CT imaging modalities is provided infra, the scope of the preferred embodiments includes any of a variety of imaging modalities that, either presently or prospectively, (i) are amenable to CAD analysis, and (ii) are accommodated by the DICOM standard (or other medical imaging standard) from a CAD perspective. Prospective examples may include magnetic resonance imaging (MRI), positron emission tomography (PET), single-photon emission computed tomography (SPECT), and ultrasound, as well as less conventional medical imaging modalities such as thermography, electrical conductivity-based modalities, etc.

Among the recent CAD-related additions to the DICOM standard are additional Information Object Definitions (IODs), including the Mammography CAD Structured Report (SR) IOD and the Chest CAD SR IOD (PS 3.3, Annexes A.35.5, A.35.6). The Mammography and Chest CAD SR IODs are used to convey the detection and analysis results of mammography and chest CAD systems, respectively. The content may include textual and a variety of coded information, numeric measurement values, references to the image data from which the CAD results were obtained, and spatial regions of interest within that referenced image data. The Mammography/Chest CAD SR IODs accommodate data not only for presentation to the clinician, but also data that may be solely for use in subsequent mammography/chest CAD analyses.

The contents and formatting of the Mammography and Chest CAD SR IODs are constrained according to CAD-related additions to PS 3.16 in the form of templates, and context groups for the coded terminology. For example, the Mammography CAD SR IOD is constructed according to the "Template ID (TID) 4000 Mammography CAD Document Root Template" which, in turn, can implicate subordinate templates as needed, the subordinate templates having names such as "TID 4001 Mammography CAD Overall Impression/Recommendation Template," "TID 4009 Mammography CAD Individual Calcification Template," "TID 4010 Mammography CAD Calcification Cluster Template," and "TID 4011 Mammography CAD Density Template." Likewise, the Chest CAD SR IOD is constructed according to the "TID 4100 Chest CAD Document Root Template" which, in turn, can implicate subordinate templates such as "TID 4101 Chest CAD Findings Summary Template," "TID 4102 Chest CAD Composite Feature Template," and "TID 4105 Chest CAD Descriptors." Further information on the Mammography and Chest CAD SR IODs are provided in PS 3.3 at Annexes L and M, respectively.

Other additions to the DICOM standard made to accommodate CAD include the addition of specified Service-Object Pair (SOP) Classes. As known in the art, a SOP Class is a union of a specific set of DICOM Message Service Elements (DIMSEs) and a related IOD which completely defines a precise context for communication. For accommodation of CAD, there are now two Structured Reporting Storage SOP Classes—the Mammography CAD SR SOP Class and the Chest CAD SR SOP Class—instances of which transfer Mammography CAD SR Object Instances and Chest CAD SR Object Instances, respectively, from one device to another. (PS 3.4, Annexes B.5, O). There is also an additional Structured Reporting Media Storage SOP Class for each of the Mammography and Chest CAD SR IODs, instances of which are interchange and offline storage of Mammography CAD SR Object Instances and Chest CAD SR Object Instances, respectively (PS 3.4, Annex I). Finally, there are also additional SOP Class Unique Identifiers (UIDs) for the additional SOP Classes (PS 3.6, Annex A).

For clarity of presentation herein, where convenient, an information object (IO) or information object instance (IOI) shall be referred to independently of the SOP Class or SOP Instance of which they may be a part. The formation or presence of the appropriate SOP Class or SOP Instance can be inferred from the identity of the IO or IOI being described, together with the action being taken and/or the descriptive context. Also for clarity of presentation herein, where convenient, treatment of IOs or IOIs is without regard to their classification as normalized or composite, it being understood that their appropriate type, as well as the appropriate corresponding DIMSEs, SOP Classes, SOP Instances, etc., can be likewise inferred.

A typical configuration for a DICOM-based medical imaging system having CAD analysis features includes an image acquisition system (IAS), a CAD processing unit, and a viewing workstation (VWS). The IAS, CAD processing unit, and VWS are usually connected by a network, most commonly a TCP/IP based network, having sufficient bandwidth to accommodate transfer of medical images thereamong. The IAS is coupled to a physical image acquisition device (e.g., digital x-ray unit, CT unit, etc.) and receives the raw image data therefrom. The IAS populates the attributes of the relevant image information object, e.g., the Digital Mammography X-Ray Image Information Object or the CT Image Information Object, to form an instance of that object, which is generically referred to herein as a Source Image Information Object Instance (SI-IOI), it being understood that "Source" is substituted for the particular modality ("Digital X-Ray", "CT", etc.) as the preferred embodiments described herein extend to a variety of imaging modalities.

The SI-IOI is then transferred to the CAD processing unit, which performs CAD analysis on the digital image(s) contained in the SI-IOI. Based on the results of the CAD analysis, the CAD processing unit constructs the relevant CAD SR Information Object Instance (CAD SR-IOI), e.g., the Mammography CAD SR-IOI or the Chest CAD SR-IOI. The CAD SR-IOI is then transferred to the VWS. Depending on the particular system implementation, the original SI-IOI created by the IAS may be transferred directly from the IAS to the VWS or, alternatively, the original SI-IOI can accompany the CAD SR-IOI from the CAD processing unit to the VWS.

The VWS generates a display of the digital source image (s) contained in the SI-IOI, which are usually of diagnostic quality. The VWS also renders the CAD information contained in the CAD SR-IOI for presentation to a clinician. Rendering generally refers to the extraction of relevant CAD information from the CAD SR-IOI and the display of that information in a manner that facilitates clinician analysis of the medical image(s) upon which that CAD SR-IOI is based. In one known system, the VWS superimposes CAD markers and other CAD annotations derived from the CAD SR-IOI over the original digital images in the SI-IOI responsive to the clinician's pressing of a single toggle button. This provides a fast and easy method of offering a "second look" opportunity for the clinician in order to facilitate early detection of anatomical abnormalities.

A problem can arise, however, for market entrants or smaller enterprises seeking to market CAD processing units alone, their customers purchasing IAS and VWS units from other suppliers. More particularly, either presently or prospectively, a large enterprise having a substantial VWS market presence might harness that VWS market presence to bolster its share in the CAD processing unit market. In one scenario, this could be attempted by disabling the VWS from receiving and rendering CAD SR-IOIs, using either a software key or other disabling mechanism, unless the VWS customer also purchases their CAD processing unit from the VWS supplier. This effectively prevents the customer from purchasing their CAD processing unit from another source, because they would not be able to receive and view the results from the competing CAD processing unit in a DICOM-conforming manner. Rather, the customer would be required to view their CAD results in more awkward and workflow-inhibiting ways, such as by using paper CAD result printouts, or by placing an entirely additional CAD viewing workstation next to their VWS. This represents an undesirable scenario for the customer and, of course, for the provider of the competing CAD processing unit.

Another problem can be found in relation to new CAD processing capabilities as they arise, regardless of whether they are developed by a market entrant, a smaller enterprise, or a large existing enterprise. In particular, the ability of the DICOM standard to accommodate new CAD processing capabilities, in the form of appropriate CAD SR IODs, for example, can lag behind the introduction of the new CAD processing capabilities themselves. By way of example, while the DICOM standard may presently include Mammography CAD SR IODs and Chest CAD SR IODs, it may not presently include colon CAD SR IODs, bone CAD SR IODs, or, more generally, "anatomy X" SR IODs. By way of further example—although expected to be a less common scenario—a currently established CAD SR IOD might not yet accommodate a brand new form of CAD processing ability for that particular anatomical part, such as upon the discovery of new anatomical patterns shown to signify a future likelihood of disease. An enterprise wanting to market CAD processing units capable of the newest CAD capabilities would again be required to have their customers use the new machines in awkward and workflow-inhibiting ways, because existing the DICOM-conforming VWS units would not be capable of receiving and rendering the CAD results therefrom. Alternatively, the new CAD processing units and the existing VWS units would need private mutual modifications, most likely of the non-conforming variety, in order to accommodate transfer and rendering of the CAD results, which is generally undesirable in the long term.

Another problem can arise in that, even if the VWS manufacturer is not purposely attempting to disable CAD-related communication features, their VWS can simply be incompetently or erroneously designed, tested, and/or implemented such that structured reporting communications with the CAD processing unit are hindered. Also, for any of a variety of reasons, a given VWS installation may not be sufficiently backward-compatible or forward-compatible as needed to properly achieve the needed structured reporting communications with the CAD processing unit.

One known DICOM-based medical imaging system, developed prior to the adoption by the DICOM Standards Committee of general structured reporting including the above CAD SR IODs, uses the Radio Therapy Structured Set (RTSS) to communicate CAD results from a CAD processing unit to an VWS or other DICOM system. See R2 Technology, Inc., "DICOM Conformance Statement M1000-DM, V2.3A" (February 2001). However, as stated in a warning therein, "The use of RTSS by this device does not conform to the DICOM standard, as the data in the RTSS object is not radiotherapy related." Accordingly, use of the RTSS to communicate CAD results from a CAD processing unit entails non-conforming operation of both the CAD processing unit and the VWS (or other destination device), which is generally undesirable in the long term.

Accordingly, it would be desirable to provide a method of doing business in which a CAD processing unit provider can integrate its CAD processing units into existing medical imaging systems in a DICOM-conforming manner, even where a VWS in the medical imaging system has had one or more of its DICOM CAD accommodations disabled for that CAD processing unit provider.

It would be further desirable to provide a medical imaging system in which CAD results are communicated, in a DICOM-conforming manner, from a CAD processing unit to a VWS for presentation to a clinician, even where the VWS cannot or will not properly receive or process any DICOM CAD structured reports, and/or a particular kind of DICOM CAD structured report, from the CAD processing unit.

It would be further desirable to provide a medical imaging system in which CAD results are communicated, in a DICOM-conforming manner, from a CAD processing unit to a VWS for presentation to a clinician, even where there is currently no mechanism to describe those CAD results using the current CAD accommodations of the DICOM standard, that is, when the DICOM CAD accommodations have not been amended or appended to cover the particular kind of CAD processing performed by the CAD processing unit.

SUMMARY

A method and system for communicating computer-aided detection (CAD) results in a DICOM-based medical imaging environment is provided, wherein a source image is analyzed by a CAD processing unit to generate the CAD results, the CAD results including CAD markers and CAD annotations, wherein the CAD markers are fixably integrated into the pixels of a secondary image derived from the source image, and wherein the secondary image is incorporated into a DICOM Secondary Capture Image Information Object Instance for transfer to a destination DICOM-conforming device. Preferably, the destination DICOM-conforming device is a viewing workstation, whereby a clinician can open, view, and manipulate the secondary image containing the CAD markers in a side-by-side comparison with the source image or derivative thereof. In another preferred embodiment, CAD annotations such as text-based identifiers, analyses, comments, and/or suspiciousness metrics are also fixably integrated into the pixels of the secondary image. Advantageously, CAD results are communicated to the clinician in a DICOM-conforming manner independent of whether the viewing workstation supports standard DICOM CAD accommodations, such as CAD Structured Report Objects, for the particular type of CAD results. Likewise, CAD results are communicated to the clinician in a DICOM-conforming manner even if the DICOM standard itself has not been amended or appended to accommodate the particular kind of CAD results.

In one preferred embodiment, the source image is contained within a Source Image Information Object Instance, the Source Image Information Object Instance being identified by a patient ID, a study instance UID, a series instance UID, and other information that allows unique identification thereof. The CAD processing unit includes the patient ID and the study instance UID into the Secondary Capture Image Information Object Instance. The Source Image Information Object Instance may be transferred to the viewing workstation from the CAD processing unit or, alternatively, may be transferred to the viewing workstation from another DICOM device such as an image acquisition system. Based on the patient ID and the study instance UID contained in the Secondary Capture Image Information Object Instance, the viewing workstation matches the Source Image Information Object Instance therewith. By manual, semi-automated, or automatic means the clinician is notified of the presence of the Secondary Capture Image Information Object Instance containing the secondary image. The user can view, resize, and otherwise manipulate the secondary image containing the fixably integrated CAD results on the user display of the viewing workstation. Advantageously, provided that the viewing workstation supports DICOM Secondary Capture Objects, no re-programming or other modification of the viewing workstation itself is necessary to accommodate this functionality.

In another preferred embodiment, the input to the CAD processing unit is a digital x-ray image that has been scanned and digitized from an x-ray film. When presented to the CAD processing unit, the digital x-ray image may optionally be in a non-DICOM conforming format. In such case, the CAD processing unit constructs a DICOM-conforming Source Image Information Object Instance, as well as a related Secondary Capture Image Information Object Instance that includes the secondary image containing the fixably integrated CAD results, for forwarding to the viewing workstation in a DICOM-conforming manner. Alternatively, the digital x-ray image and the CAD results may be forwarded to an adapting processor that constructs the appropriate DICOM-conforming Source Image Information Object Instance and Secondary Capture Image Information Object Instance, which are then forwarded to the viewing workstation.

In another preferred embodiment, a method of doing business is provided in a standards-based medical imaging environment comprising a first enterprise having an established market presence for viewing workstations, the first enterprise disabling one or more CAD result accommodation features of a standard medical imaging communications protocol if integrated with CAD processing units from a second enterprise, wherein the second enterprise causes its CAD processing units to fixably integrate its CAD results into the pixels of a secondary image type supported by the standard medical imaging communications protocol, the secondary image type not being specified for CAD results. Preferably, the medical imaging communications protocol is the DICOM standard, and the secondary image type corresponds to the Secondary Capture Image Information Object defined by the DICOM standard.

In another preferred embodiment, in the event that the viewing workstation is designed to be capable of receiving and processing CAD Structured Report Information Object Instances for the CAD processing capability in question, but where such capability has been disabled for a particular target CAD processing unit manufacturer, the CAD processing unit manufacturer designs its CAD processing unit to generate a CAD Structured Report Information Object Instance having a modified equipment information entity identifier. In particular, the equipment information entity identifier is assigned values not corresponding to the target CAD processing unit manufacturer, but rather to a different entity, whereby the viewing workstation receives and processes the CAD Structured Report Information Object Instance as usual, since it is not apparent that it actually came from that target CAD processing unit manufacturer. In one preferred embodiment, the equipment information entity identifier is assigned to a value extracted from the Source Image Information Object Instance. In another preferred embodiment, the equipment information entity identifier corresponds to the viewing workstation manufacturer itself. In another preferred embodiment, in the event that the viewing workstation goes so far as to disable Secondary Capture Image Information Object Instances from the target CAD processing unit manufacturer, an equipment information entity identifier contained in each Secondary Capture Image Information Object Instance is likewise modified.

DETAILED DESCRIPTION

Figure 1:
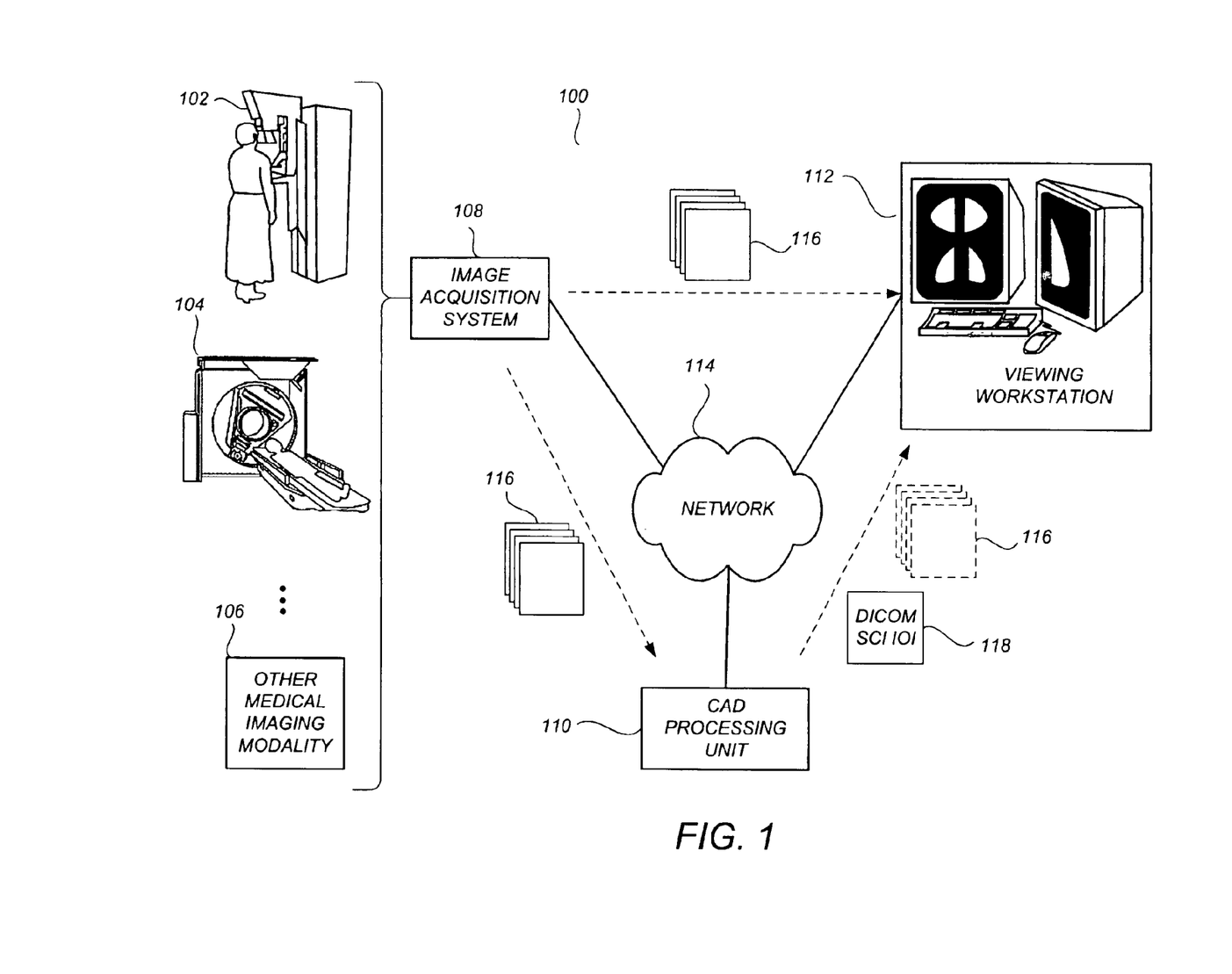
FIG. 1 illustrates a medical imaging system including a computer-aided detection (CAD) processor according to a preferred embodiment.

FIG. 1 illustrates a medical imaging system 100 according to a preferred embodiment including an image acquisition system (IAS) 108, a CAD processing unit 110, and a viewing workstation (VWS) 112 coupled to a network 114. The network 114 may comprise a local area network (LAN), a metropolitan area network (MAN), a wide area network (WAN), or generally any network capable of communicating images among the IAS 108, CAD processing unit 110, and VWS 112. It is to be appreciated that the IAS 108, CAD processing unit 110, and VWS 112 may be contained in the same building, distributed across a metropolitan area, or may even be located in different states or continents depending on the particular implementation of the medical imaging system 100. Preferably, the network 114 supports the TCP/IP protocol, which is used as the transport protocol for the DICOM standard.

Coupled to IAS 108 in FIG. 1 is a digital x-ray mammography unit 102 and a computed tomography (CT) unit 104. However, as indicated by the "other" medical imaging modality element 106, the preferred embodiments are readily extended to any of a variety of present or prospective medical imaging modalities, such as MRI, PET, SPECT, ultrasound, x-ray tomosynthesis, thermography, electrical conductivity-based modalities, and other modalities. For clarity of description, a particular example of digital x-ray mammography, and CAD processing related thereto, is described, it being understood that the scope of the preferred embodiments is readily extended to Chest CT as well as these other imaging modalities. It is also to be appreciated that IAS 108 may itself be a distributed system, may be integrated with one of the imaging units 102–106 into a monolithic image acquisition device, or may alternatively be separated therefrom by large distances and coupled via a network, without departing from the scope of the preferred embodiments.

Also shown in FIG. 1 is a conceptual diagram of four Source Image Information Object Instances (SI-IOIs) 116 being transferred from the IAS 108 to the CAD processing unit 110 over the network 114. Each SI-IOI 116 comprises identifying information including a patient ID, a study instance UID, and a series instance UID, as well as other information that uniquely identify that SI-IOI. For digital x-ray mammography, in a typical scenario in which a patent visits a clinic on a given day and gets the four standard views taken (LCC, LMLO, RCC, RMLO), there are actually four distinct SI-IOIs created, one for each view. These four SI-IOIs typically have the same patient ID and study instance UID but, depending on the particular IAS manufacturer, they might not have the same series instance UIDs.

Likewise, for a typical scenario in chest CT imaging, there are typically many distinct SI-IOIs created, one for each tomographic slice obtained, all having the same patient ID and study instance UID but possibly having different series instance UIDs depending on the IAS manufacturer. For ultrasound and MRI, it is more common that there be a single SI-IOI containing all of the related ultrasound or MRI slice images, which is termed a multi-frame SI-IOI.

However, it is to be appreciated that the preferred embodiments described herein are applicable to any of these situations and other situations, with the term SI-IOI (e.g., SI-IOI 116) being used herein to refer to any of the following, unless otherwise indicated: a lone single-frame SI-IOI, a group of related single-frame SI-IOIs, a lone multi-frame SI-IOI, or a group of related multi-frame SI-IOIs, or any combination thereof.

Figure 7:
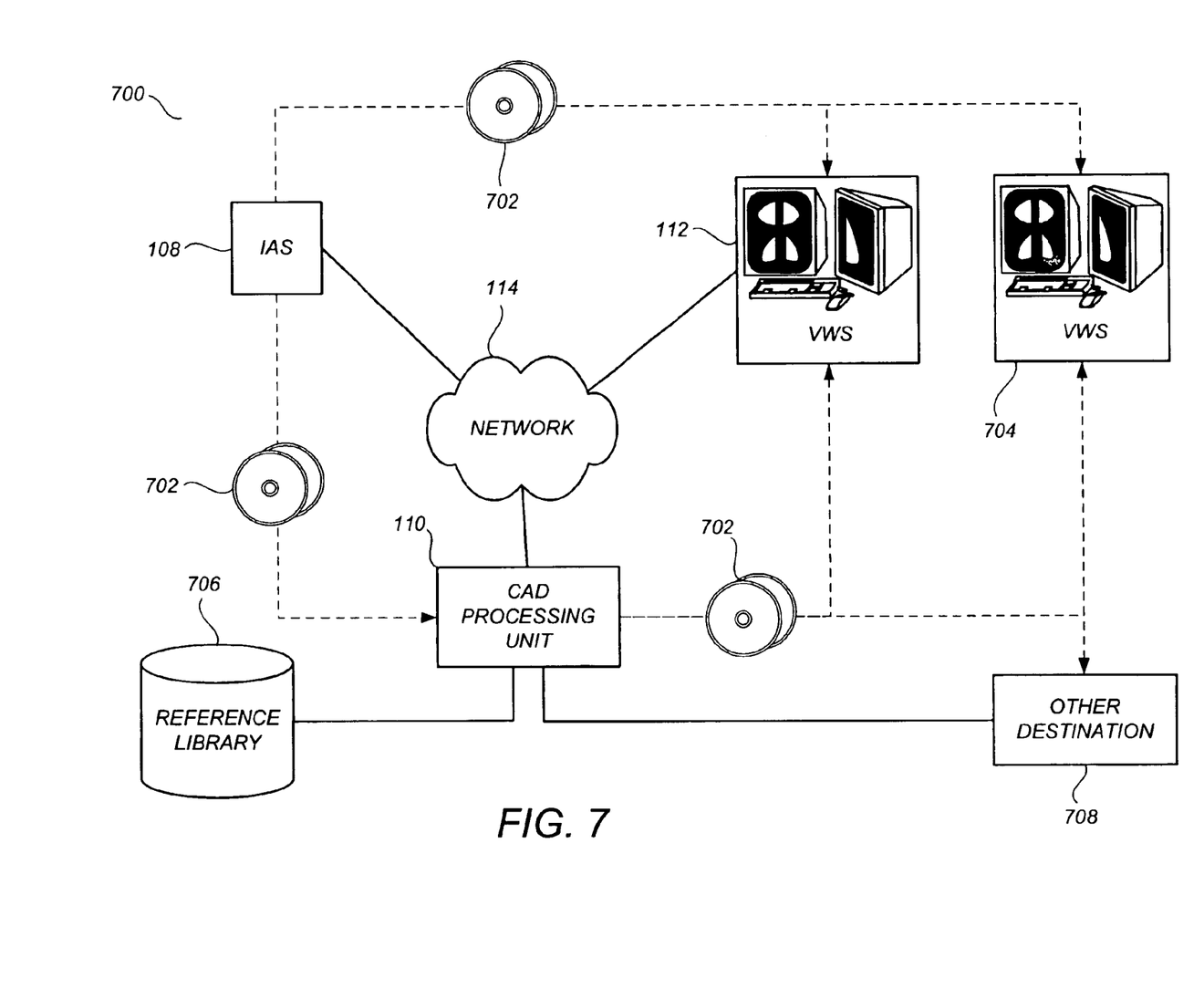
FIG. 7 illustrates a medical imaging system including a CAD processing unit and an image reference library according to a preferred embodiment.

Preferably, as indicated in FIG. 1, the SI-IOI 116 is also sent directly from the IAS 106 to the VWS 112, although this can vary according to the desired configuration. If not sent from the IAS 108, the SI-IOI 116 can be forwarded from the CAD processor 110 along with a DICOM Secondary Capture Image Information Object Instance (SCI-IOI) 118. It is to be appreciated that other devices, such as storage devices or other auxiliary devices, may be included along the data paths shown in FIG. 1, and also that many different timing schemes (real-time transfer, non-real-time transfer) can be implemented without departing from the scope of the preferred embodiments. One example of an alternative configuration is illustrated in FIG. 7, infra, wherein information is optionally transferred among two or more of the system components by compact disks, DVDs, or other tangible storage media.

It is to be further appreciated that digital image(s) in the SI-IOI 116 can be modified, filtered, or otherwise manipulated by the IAS 108 prior to being sent to the VWS 112, or may be manipulated along the path from IAS 108 to VWS 112 by an intermediate device (not shown), resulting in one or more of what are termed herein derivative viewing images. As known in the art, the derivative viewing images would most often be contained in separate Image Information Object Instances than the SI-IOI 116, but having the same patient ID and study instance UID, and would arrive separately at the VWS 112. Alternatively or in conjunction therewith, the source image(s) and/or derivative viewing image(s) may be manipulated by the VWS 112 itself prior to display.

Figure 2:
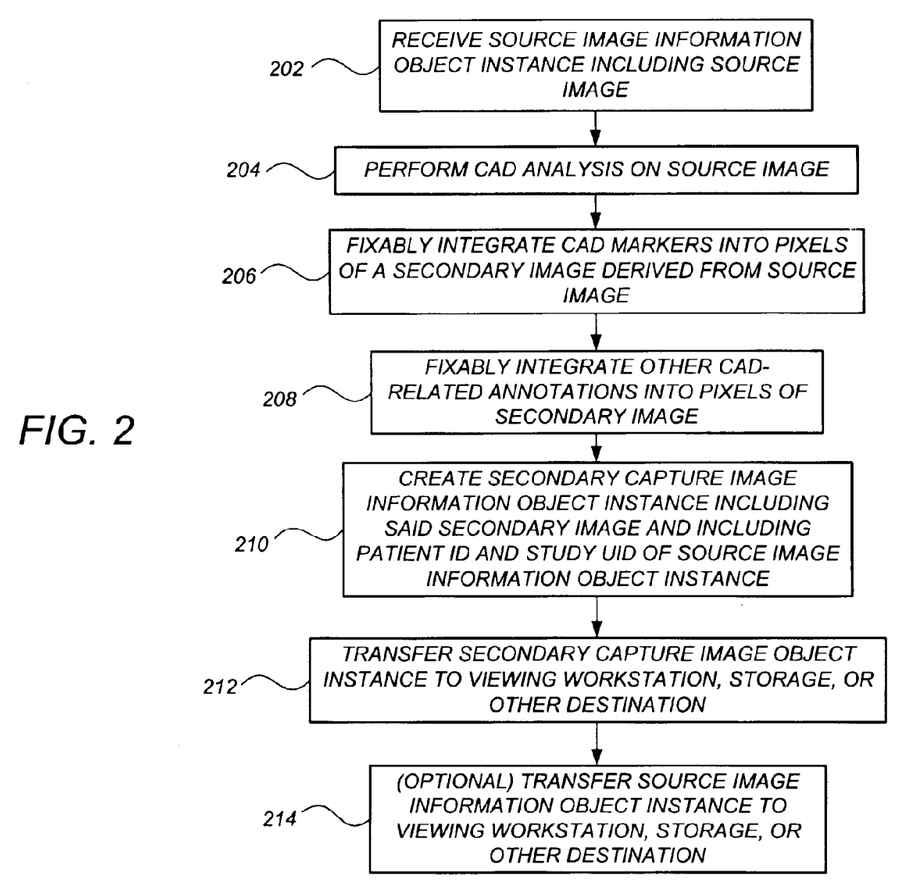
FIG. 2 illustrates steps for CAD results communication in a DICOM environment according to a preferred embodiment.

FIG. 2 illustrates steps taken by the CAD processing unit 110 according to a preferred embodiment. At step 202, the SI-IOI 116 is received from the IAS 108. At step 204, CAD analysis is performed thereon. In the case of digital x-ray mammography, for example, the CAD processing unit would extract a digital image contained in the SI-IOI 116 and search for suspicious breast masses, microcalcification clusters, or other abnormalities therein that may be evidence of breast cancer. At step 206, the CAD processing unit fixably integrates CAD markers into pixels of a secondary image derived from one or more of the source images.

The secondary image comprises an image of at least a portion of the anatomical part contained in the source image. The secondary image is preferably a flat image, and the CAD markers are "burned in" to the pixels of the flat image near the lesion locations. Each pixel location that is part of a CAD marker actually loses it pixel value (or, in the case of a color image, values) because that pixel was forcibly turned to pure black, pure white, or some other pixel value according to the CAD marking scheme. Advantageously, the VWS could never "detect" that the secondary image actually contains CAD markers, absent the unlikely event that intelligent "marker-detection algorithms" were put in place by the VWS manufacturer. Thus, using this preferred embodiment, a CAD processing competitor can effectively combat a situation such as that described supra in which a VWS manufacturer attempts to shut out that CAD processing competitor by deactivating formal DICOM CAD-accommodating features of their VWS if it is coupled to a CAD processing unit from that CAD processing competitor.

Even in the absence of such a contentious competitive/anticompetitive environment, the SCI-IOI containing the secondary image can be used to communicate newly developed CAD result types that the current CAD accommodations of the DICOM standard have no mechanism to convey. Indeed, in one preferred embodiment, the SCI-IOI containing the secondary image can be sent in addition to the standard CAD SR-IOI, and the VWS can both (i) render the CAD SR-IOI and (ii) allow the user to display and manipulate the secondary image contained in the SCI-IOI. The SCI-IOI containing the secondary image can also be used if the relevant CAD SR-IOIs cannot be used due to design failures, lack of backward- or forward-compatibility, or any of a variety of other anomalous situations.

At step 208, the CAD processing unit fixably integrates or "burns" other CAD-related annotations, such as textual notes or alphanumeric lesion suspiciousness levels, into the pixels of the secondary image. Thus, the pixel locations corresponding to CAD annotations and CAD markers irretrievably lose their underlying image data. For example, if a given pixel location happens to be at a location corresponding the dot in the "i" of a textual annotation, that underlying image value is lost and replaced by a zero (for black) or other fixed value.

At step 210, the Secondary Capture Image Information Object Instance (SCI-IOI) 118 is created that contains the secondary image. Depending on the nature of the SI-IOI 116, the CAD processing algorithms, and/or the nature of the desired outcomes, there may be more than one SCI-IOI, and indeed there may be many separate SCI-IOIs depending on how many different annotated images are desired. Each SCI-IOI, however, should contain the patient ID and the study instance UID of the SI-IOI 116 necessary for the VWS or other destination device to match that SCI-IOI with the corresponding source image(s) and/or derived viewing image(s). The Referenced Image Sequence or Source Image Sequence attribute can be populated in the SCI-IOI, with the SOP Class UID, SOP Instance UID, and Frame Number of the one or more SI-IOIs from which the SCI-IOI was derived. Although described in terms of using the patient ID and study instance UID to match the secondary image of SCI-IOI 118 with the source image of SI-IOI 116 and/or derivative viewing image, the scope of the preferred embodiments is not so limited, and includes any of a variety of other matching scenarios sufficient to match up these image, as could be readily implemented by one skilled in the art in view of the present disclosure.

At step 212, the SCI IOI 116 is transferred to the VWS 112, or other destination device, such as a storage device. Optionally, as discussed supra, at step 214 the SI-IOI 116 is also transferred from the CAD processing unit to the VWS 112.

Figure 3:
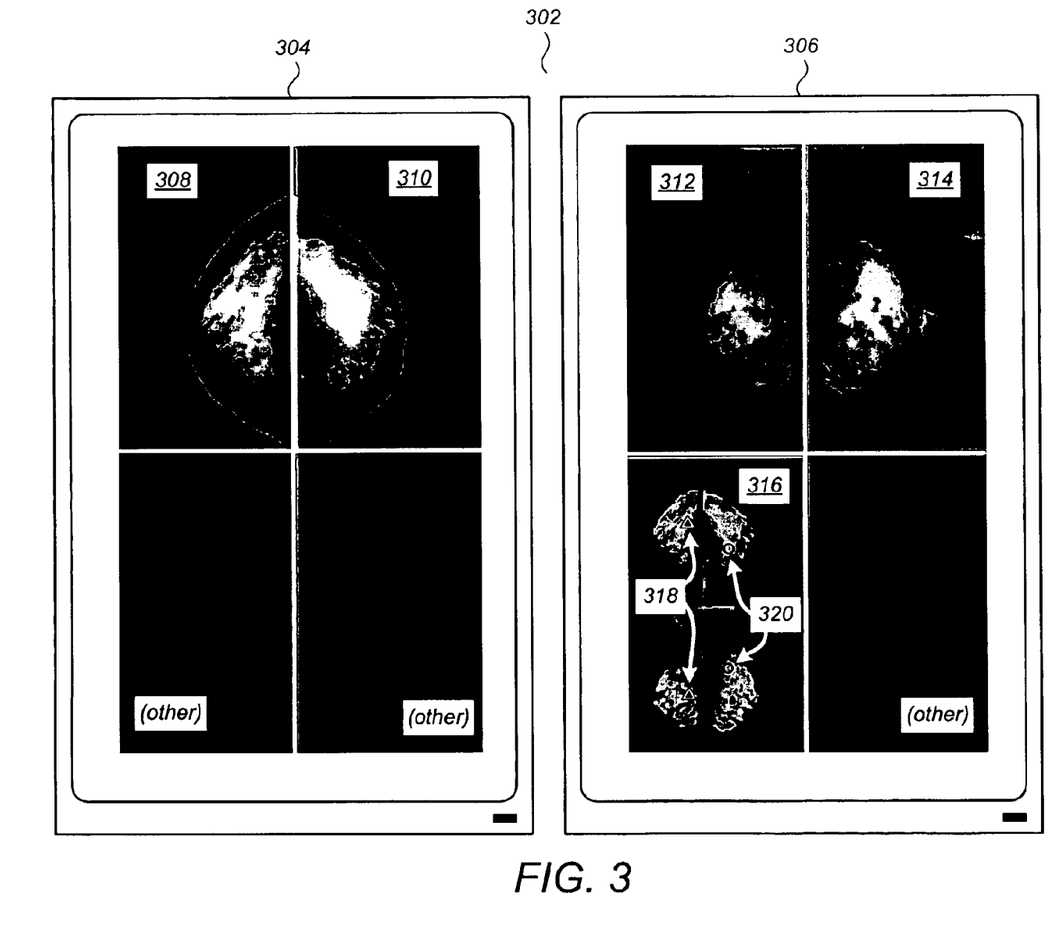
FIG. 3 illustrates a viewing workstation displaying a secondary image having fixably integrated CAD markers, the secondary image being displayed side-by-side with source medical images from which the CAD results were derived or derivative viewing images derived from the source medical images.

FIG. 3 illustrates an example of a display of a viewing workstation (VWS) 302 that may be used in the system of FIG. 1, comprising a left monitor 304 and a right monitor 306. The VWS 302 is displaying, by way of example and not by way of limitation, one of a variety of different hanging protocols for viewing the source medical image(s)—and/or derivative viewing image(s)—along with the secondary image(s) containing the CAD results. Left monitor 304 displays source RCC and LCC images 308 and 310, respectively, while right monitor 306 displays source RMLO and LMLO images 312 and 314, respectively. Alternatively or in conjunction therewith, any of the images 308–314 may comprise derivative viewing images computed from the source images, as described supra. Included on both monitors is "other" space that could be used for appropriate user controls or notifications (not shown), which include a notification, preferably iconic, to the clinician that an SCI-IOI is available. Upon clicking the icon or otherwise invoking the SCI-IOI, the user is presented with the secondary image 316, which comprises at least one image of at least a portion of the anatomical part being displayed in any of images 308–314, and which includes fixably integrated CAD markers 318 and 320 indicating a suspicious density and a suspicious microcalcification cluster, respectively. In accordance with commonly provided VWS features, the user is permitted to shift the different window locations around and resize them as needed.

Preferably, the secondary image 316 is of lower resolution, generally lower quality, and/or smaller size than the original images 308–314, although the scope of the preferred embodiments is not so limited. Because it should only be used as a "second look," and should not be the sole basis of a diagnosis, the secondary image 316 should not need to be of equal or superior quality to the original images 308–314. Moreover, as an inferior-quality image, the secondary image 316 will not tempt the clinician to use it as a primary diagnosis tool, and also takes up less storage space and is faster to transmit over the network 114. However, it is to be appreciated that in some alternative embodiments the secondary image could be of diagnostic quality without departing from the scope of the preferred embodiments. In the preferred embodiment of FIG. 3, the secondary image 316 is a single, flat image file comprising four quadrants containing minified versions of the original image according to the hanging protocol shown.

Figure 4:
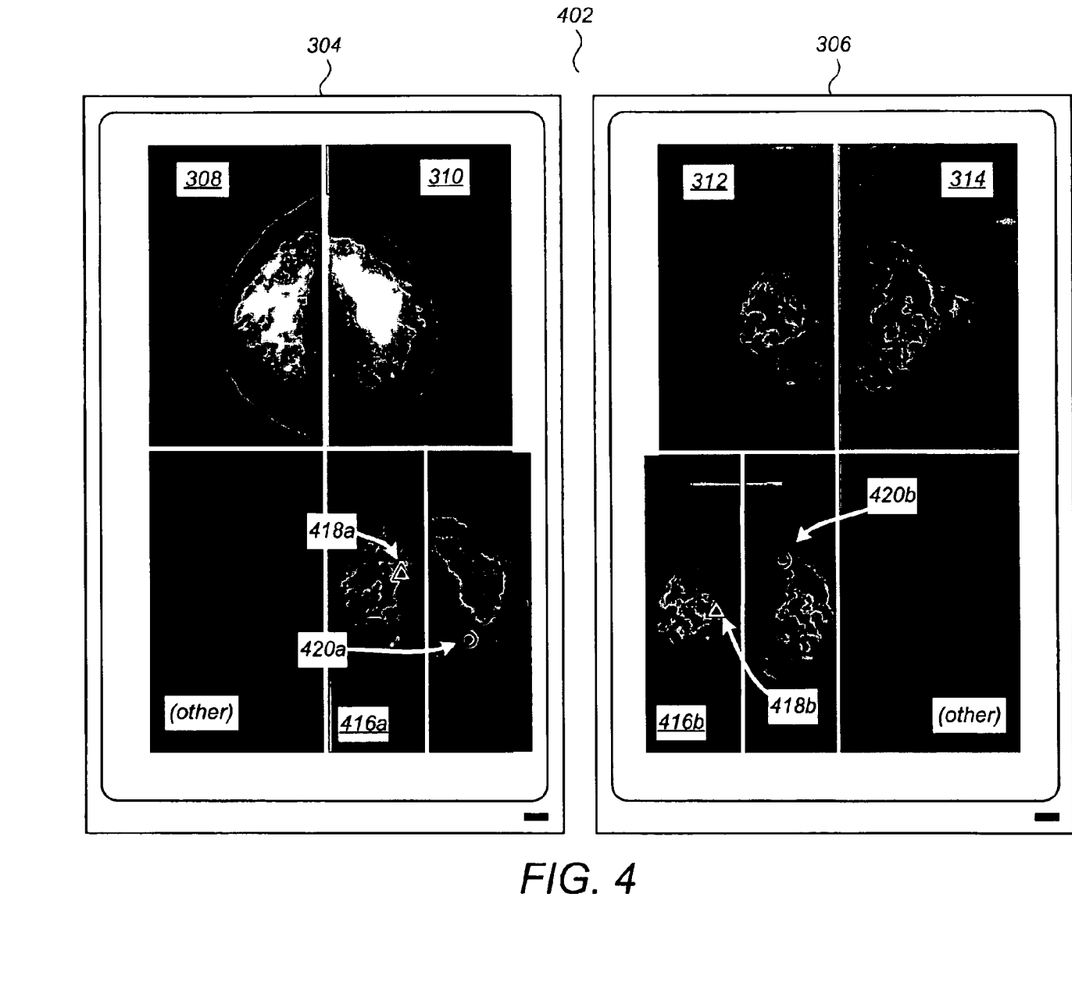
FIG. 4 illustrates a viewing workstation displaying two secondary images having fixably integrated CAD markers, the secondary images being displayed side-by-side with source medical images from which the CAD results were derived or derivative viewing images derived from the source medical images.

FIG. 4 illustrates an example of a display of a viewing workstation (VWS) 402 that may be used in the system of FIG. 1, comprising elements 304–314 similar to those in the VWS 302 of FIG. 3, supra, but comprising two secondary images 416a and 416b showing CAD markers 418a and 418b for a suspicious density, and showing CAD markers 420a and 420b for a suspicious microcalcification cluster, according to the hanging protocol shown. In this preferred embodiment, the secondary images 416a and 416b are incorporated into separate SCI-IOIs for transfer from the CAD processing unit 110 to the VWS 112. The clinician is provided with two separate notification icons and can separately open and manipulate the secondary images. In another preferred embodiment (not shown), there can be four different secondary images provided in four different SCI-IOIs, each showing a single view of the breast, and so on.

Figure 5:
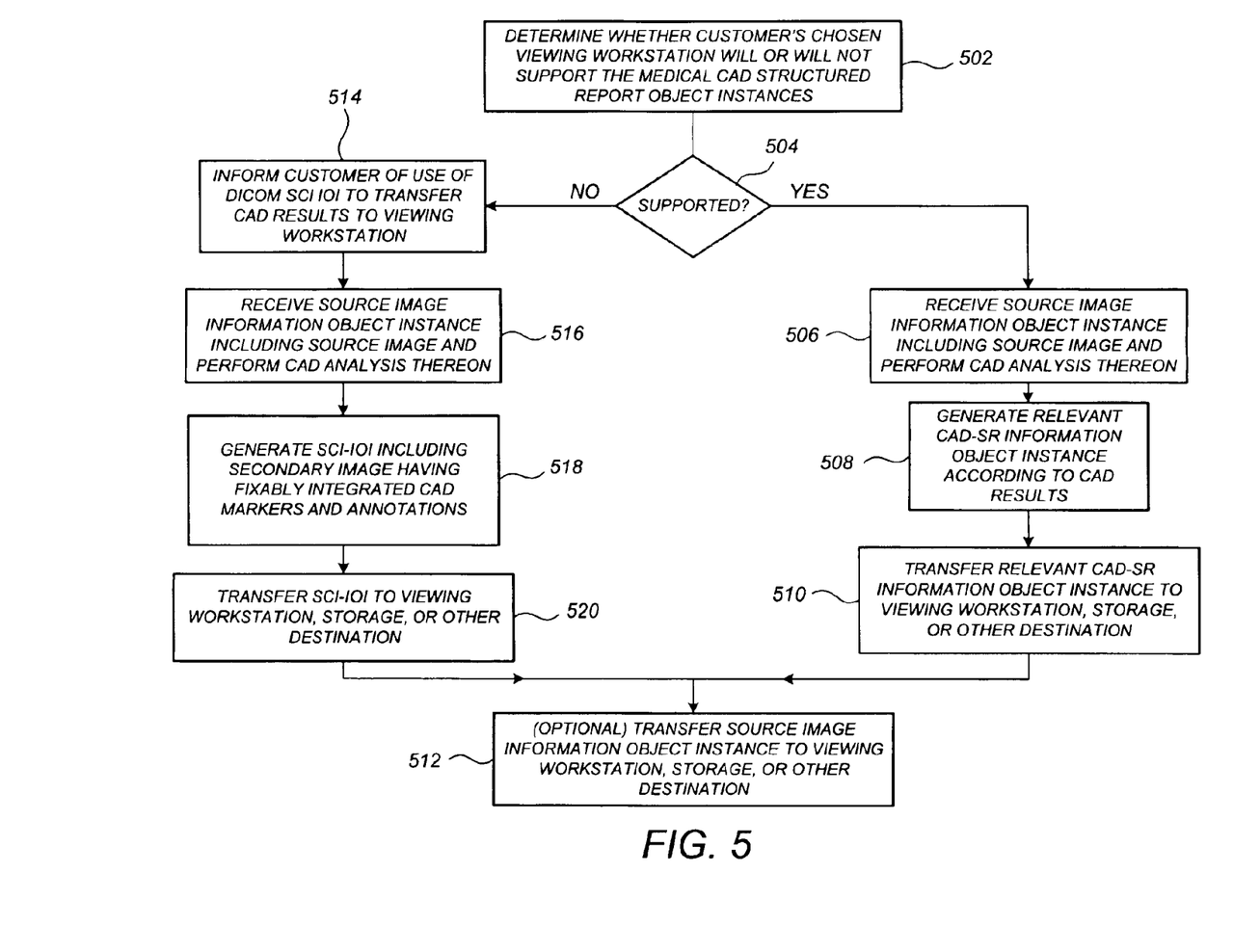
FIG. 5 illustrates steps in a method of doing business according to a preferred embodiment.

FIG. 5 illustrates steps in a method of doing business in a standards-based medical imaging environment, with particular application to a CAD processing unit manufacturer that is not also a direct provider of VWS units. At step 502, facts are gathered to determined whether the customer's chosen VWS supports the CAD-accommodating features of the DICOM standard, such as the Mammography CAD SR IOD in the case of x-ray mammography, or such as the Chest CAD SR IOD in the case of chest CT. These facts can be gathered by reviewing the DICOM Conformance Statement of the VWS, which is required for all devices purported to at least partially conform to DICOM. Alternatively or in conjunction therewith, the facts for step 502 can be gathered by empirical testing of off-the-shelf version of the VWS, or by examining other product literature.

In another preferred embodiment, the determination can be dynamically made by the CAD processing unit 110 itself. Each time the CAD processing unit 110 establishes a DICOM association with the VWS, negotiation of accepted SOP Classes and Transfer Syntaxes (i.e., Presentation Context) is a required part of the association negotiation. The Service Class User (SCU—in this case, the CAD processing unit 110) requests a list of presentation contexts in an Association Request, and the Service Class Provider (SCP—in this case, the VWS 112) responds with accepted/rejected for each presentation context in the list, in an Association Acceptance or Rejection response. In this manner, the CAD processing unit can automatically determine whether the VWS 112 supports the relevant CAD SR IOD.

If it is determined at step 504 that the relevant CAD SR IOD is indeed supported by the VWS, then after receiving the SI-IOI and doing the CAD processing at step 506, the CAD processing unit generates at step 508 an instance of the relevant CAD SR Information Object Instance (CAD SR-IOI) and, at step 510, transfers it to the VWS. The CAD SR-IOI includes the same patient ID and study UID as the SI-IOI, but will usually have a different series UID. Optionally, at step 512, the original IIOI received by the CAD processing unit is also transferred to the VWS.

However, if it is determined at step 504 that the relevant CAD SR IOD is not supported by the VWS (or has not yet been defined), then at step 514 the customer is informed that the CAD processing unit will be providing CAD results encapsulated within SCI-IOIs at the VWS. This can be done manually by placement in the CAD processing unit user manual or literature. Alternatively, this can be done as part of the marketing, sales, or customer training process. Even in the event that the clinician is not advised prior to VWS use, it is possible that the presence of an SCI-IOI notification icon will cause them to open the icon to learn of the SCI-IOI contents. Steps 516–520 proceed in a manner similar to steps 202–212 of FIG. 2 for generating and transferring the SCI-IOI containing the secondary image having fixably integrated CAD annotations.

According to one preferred embodiment, the steps 502–520 are carried out dynamically for every case by automatically performing the conformance inquiry at step 504. This allows the CAD processing unit provider to avoid the need to make changes to the software of the unit in the event that the capabilities of the VWS are changed for business or technical reasons by the VWS manufacturer. This would be particularly advantageous for a scenario in which a newer or different CAD processing capability, not currently accommodated by the DICOM standard, is introduced into the market. In this case, once the DICOM Standards Committee has appended or amended the DICOM standard appropriately, the CAD processing unit manufacturer can program that relevant CAD SR IOD (and related changes) into its CAD processing units. Then, after the VWS manufacturer has "caught up" with the new technique, the CAD processing unit can automatically switch over from the Secondary Capture Image IOI method to the relevant CAD SR IOD method without requiring further effort or vigilance by the CAD processing unit manufacturer. Thus, adaptation can be achieved by system configuration rather than fixed software release.

Figure 6:
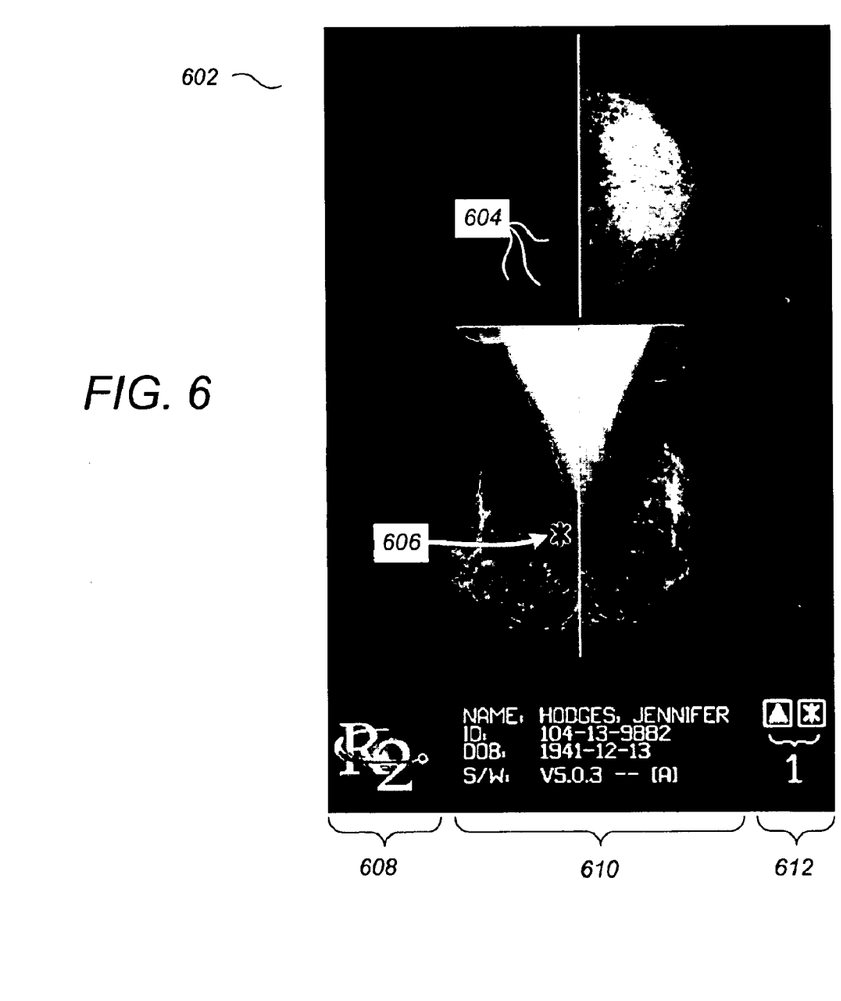
FIG. 6 illustrates a secondary image including fixably integrated CAD markers and CAD annotations according to a preferred embodiment.

FIG. 6 illustrates an example of another secondary image 602 according to a preferred embodiment. The secondary image 602 comprises one or more images 604 of at least a portion of the anatomical part that was contained in the source image of the SI-IOI, and further comprises a "burned in" CAD marker 606. Also "burned in" to the secondary image 602 is (i) a graphical symbol 608 indicating the source of origin of the CAD processing unit used to analyze the source image, (ii) an annotation text field 610 identifying key information about the patient and the CAD software version, and (iii) a result key 612. The result key 612 shows a "1" indicating that the clinician should look for a single CAD marker. The result key 612 shows a solid frame around a triangle to communicate that the microcalcification detection algorithm of the CAD processing unit terminated properly, and shows a solid frame around an asterisk shape to communicate that the mass detection algorithm of the CAD processing unit terminated properly. These frames would be dotted lines for abnormal CAD algorithm termination. Notably, the graphical and textual information is not stored in ASCII or other symbolic format, but rather is "burned in" or fixably integrated into the pixel values of the secondary image 602.

FIG. 7 illustrates a medical imaging system 700 according to a preferred embodiment, similar to the medical imaging system 100 of FIG. 1, supra, further comprising a VWS 704 not connected to the network 114, and further comprising a reference library database 706 coupled to the CAD processing unit 110. As indicated in FIG. 7, information such as the SI-IOIs and SCI-IOIs is optionally transferred among two or more of the system components by physical movement of compact disks or DVDs 702 or other tangible storage media, rather than by using network 114. An "other" destination component 708 is included to signify that there are a variety of downstream components (paper printers, film printers, storage devices, etc.) that may use the secondary images/SCI-IOIs without departing from the scope of the preferred embodiments.

The reference library 706 is configured to store large amounts of historical mammographic data (or other image data) from a variety of patients, preferably with known diagnoses. As part of its CAD algorithms, the CAD processing unit 110 can compare a current suspicious location with similar anatomical abnormalities taken from the historical data. The historical data can be from the current patient and/or a large population of patients. An example of a reference library is presented in US 2002/0043729 A1, published on Nov. 22, 2001 (Giger et. al.), which is incorporated by reference herein. According to a preferred embodiment, the secondary image of the SCI-IOI further comprises several frames and/or mini-frames of data taken from the reference library in any of a variety of configurations as described in US 2002/0043729 A1, all of this information being "burned" or fixably integrated into the secondary image. In one preferred embodiment, the secondary image comprises an overall picture of the anatomical part in question, and a plurality of mini-frames at its periphery with close-ups of suspicious locations, images from the reference library 706, etc. This is but one example of how, in accordance with a preferred embodiment, an advanced CAD-related diagnostic technique or capability can be effectively communicated to the clinician, independent of whether the DICOM standard does, or does not, support such CAD-related abilities in its CAD accommodations as currently specified.

Figure 8:
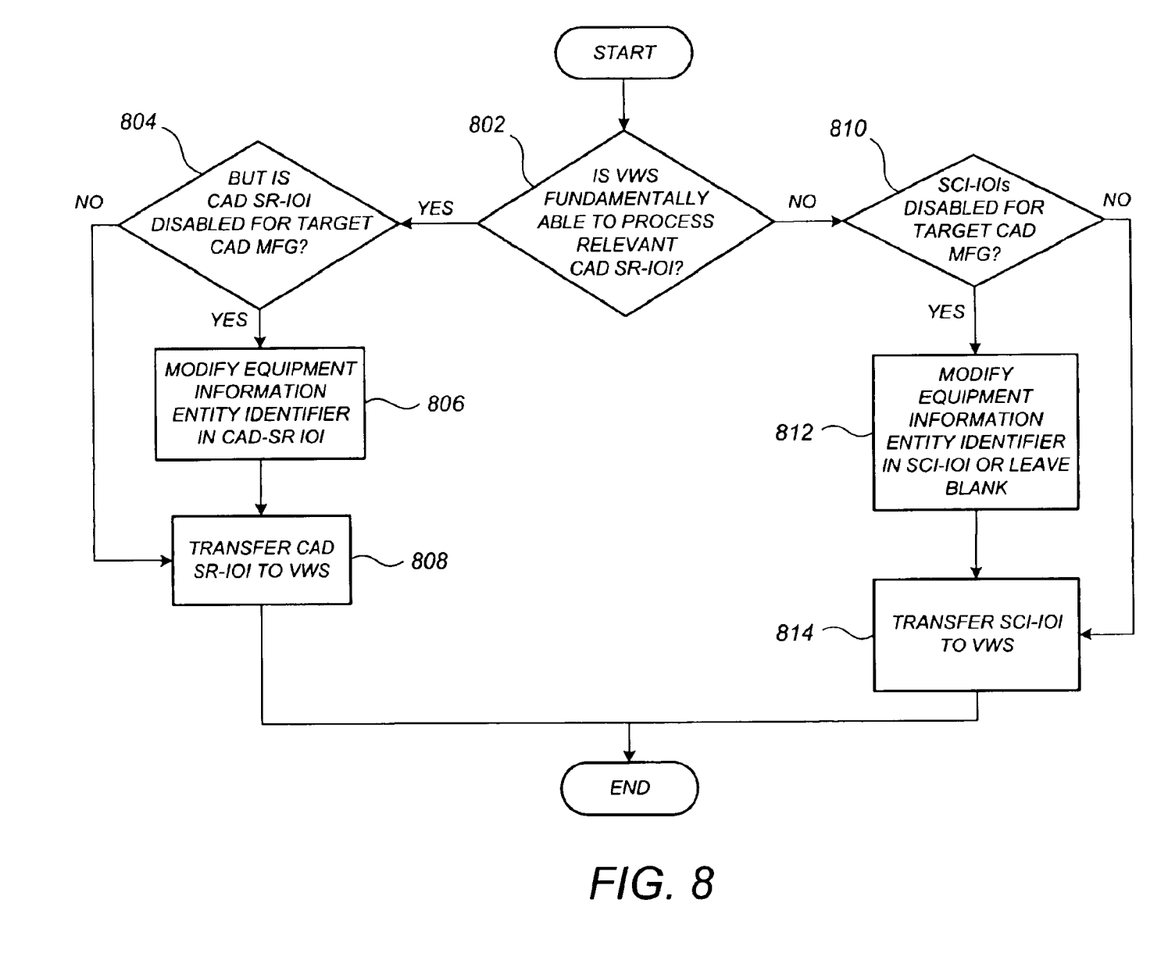
FIG. 8 illustrates a method of doing business including steps for CAD results communication in a DICOM environment according to a preferred embodiment.

FIG. 8 illustrates a method of doing business including steps for CAD results communication in a DICOM environment according to a preferred embodiment. As used herein, a target CAD manufacturer is a CAD processing unit provider that another enterprise having an established presence in the VWS market is trying to "shut out" by disabling CAD communications therewith. At step 802, it is determined whether the VWS possesses the fundamental ability to receive and process CAD Structured Report Information Object Instances for the CAD processing capability in question. If not, then at step 810, it is determined whether the VWS has disabled SCI-IOIs if they were generated from the target CAD manufacturer, and if not, then at step 814 an SCI-IOI constructed according to FIG. 2 and having "burned in" CAD markers and annotations is transmitted to the VWS. If at step 810 it is determined that the VWS manufacturer has gone so far as to disable SCI-IOIs generated from the target CAD manufacturer, then at step 812 the SCI-IOI is modified, if necessary, to ensure that the equipment information entity identifier either (i) does not contain any reference to a Secondary Capture Device's Manufacturer, Manufacturer's Model Name, or Software Version, or (ii) if it does contains one or more of such identifiers, that these identifiers do not implicate the target CAD manufacturer. The DICOM specification makes the above three specific entries optional in the SCI-IOI.

As used herein, a device is still DICOM conforming even if there is some indirection involved in a source-of-origin identifier of an IOI or SOP Instance, as these indirections are business rather than technically or medically oriented. This is distinguished from the non-conforming RTSS example presented supra, in which the RTSS was used for an entirely different medical purpose than that for which it was specified.

If, at step 802, it is determined that the viewing workstation is indeed fundamentally capable of receiving and processing CAD Structured Report Information Object Instances for the CAD processing capability in question, it is then determined at step 804 whether such capability has been disabled for the target CAD manufacturer. If not, then at step 808, a CAD SR-IOI having its equipment information identifier populated with the identity of the target CAD manufacturer (who, it has just been determined, is not a actually a "target" in this particular instance) is transferred to the VWS. But if so, then at step 806 the equipment information identifier is modified such that at least its (mandatory) Manufacturer identifier is redirected or spoofed to that of another manufacturer, and optionally the (optional) Manufacturer's Model Name and/or Software Version identifier is also similarly redirected. In one preferred embodiment, the Manufacturer identifier is spoofed to that of the IAS if the IAS is not the same as the target CAD manufacturer, and in another preferred is spoofed to that of the VWS manufacturer itself.

Whereas many alterations and modifications of the present invention will no doubt become apparent to a person of ordinary skill in the art after having read the foregoing description, it is to be understood that the particular embodiments shown and described by way of illustration are in no way intended to be considered limiting. By way of example, although detailed supra in terms of the DICOM standard, the preferred embodiments are readily applicable to any medical imaging standard having a first channel, object, or service definition directed to CAD results communication and a second channel, object, or service definition directed to accommodating secondary image types. By way of further example, in an optional preferred embodiment, the VWS can be programmed to completely skip over any case in which the number of CAD markers is zero, such that the clinician does not even see the source, secondary, or derivative viewing images at all, whereby the clinician workload and medical enterprise costs are substantially reduced. The number of CAD markers generated can be determined by accessing the appropriate CAD SR-IOI attribute, and/or by running an optical character recognition (OCR) algorithm on the result key 612 and/or or a marker detection algorithm on the overall secondary image.

By way of even further example, while described above in terms of softcopy workstations, the scope of the preferred embodiments also includes making hardcopies of the secondary images on paper or film, archiving of the SCI-IOIs, and generally any of a variety of possible downstream uses for the secondary images/SCI-IOIs. Therefore, reference to the details of the preferred embodiments are not intended to limit their scope, which is limited only by the scope of the claims set forth below.

What is claimed is:

1. A method for computer-aided detection (CAD) of anatomical abnormalities, comprising:
   receiving a first medical image of an anatomical part of a human body;
   processing the first medical image to detect anatomical abnormalities therein;
   forming a second medical image including at least a portion of the anatomical part, said second medical image having CAD markers fixably integrated therein at pixel locations corresponding to said detected anatomical abnormalities;
   incorporating said second medical image into a DICOM Secondary Capture Image Information Object Instance; and
   transferring said DICOM Secondary Capture Image Information Object Instance to a destination device.

2. The method of claim 1, said destination device being a viewing workstation, further comprising:
   extracting said second medical image from said DICOM Secondary Capture Image Information Object Instance;
   receiving a third medical image at said viewing workstation, said third medical image being derived from said first medical image; and
   concurrently displaying said second medical image and said third medical image on said viewing workstation.

3. The method of claim 2, said second medical image further comprising CAD annotations fixably integrated into pixels thereof, said CAD annotations including textual annotations.

4. The method of claim 3, wherein said first and third medical images are of diagnostic quality, and wherein said second medical image is of less-than-diagnostic quality.

5. The method of claim 4, further comprising:
   retrieving a fourth medical image from a reference library database, said reference library database comprising images of anatomical parts of the human body having known diagnoses; and
   prior to said transferring step, fixably integrating the pixels of said fourth medical image into the pixels of said second medical image.

6. The method of claim 1, wherein said destination device is a DICOM-conforming device, and wherein said destination device is selected from the group consisting of: a viewing workstation, an image archiving system, and a hardcopy printer.

7. The method of claim 6, wherein said step of transferring is performed over an electronic data communications network using the TCP/IP protocol.

8. The method of claim 6, wherein said step of transferring is performed using a tangible, portable storage medium.

9. The method of claim 8, wherein said storage medium is selected from the group consisting of: a DVD, a CD, an optical storage medium other than a DVD or CD, a magnetic tape, and a portable flash memory device.

10. The method of claim 1, further comprising:
    incorporating information relating to said detected anatomical abnormalities into a DICOM Computer Aided Detection Structured Report Information Object Instance; and
    transferring said DICOM Computer Aided Detection Structured Report Information Object Instance to said destination device.

11. The method of claim 10, said destination device being a viewing workstation, further comprising:
    extracting said second medical image from said DICOM Secondary Capture Image Information Object Instance;
    receiving a third medical image at said viewing workstation, said third medical image being derived from said first medical image;
    receiving said DICOM Computer Aided Detection Structured Report Information Object Instance at said viewing workstation;
    displaying said second medical image and said third medical image on said viewing workstation; and
    rendering said DICOM Computer Aided Detection Structured Report Information Object Instance on said workstation.

12. The method of claim 11, wherein said second medical image, said third medical image, and said rendering of said DICOM Computer Aided Detection Structured Report Information Object Instance are concurrently displayed on said workstation.

13. The method of claim 11, said DICOM Computer Aided Detection Structured Report Information Object Instance including an equipment information entity identifier, said method further comprising setting said equipment information entity identifier to a substitute value not indicative of a manufacturer of a CAD system that performed said processing.

14. The method of claim 1, wherein said receiving said first medical image comprises receiving a Source Image Information Object Instance from a DICOM-conforming source device, the Source Image Information Object Instance comprising said first medical image.

15. The method of claim 1, wherein said step of receiving said first medical image comprises:
    receiving a film-based image of said anatomical part of the human body; and
    digitizing said film-based image to form said first medical image.

16. A method for computer-aided detection (CAD) of anatomical abnormalities, comprising:
    receiving a first medical image of an anatomical part of a human body;
    processing the first medical image to detect anatomical abnormalities therein;
    forming a second medical image including at least a portion of the anatomical part, said second medical image having CAD markers fixably integrated therein at pixel locations corresponding to said detected anatomical abnormalities;
    incorporating said second medical image into a DICOM Secondary Capture Image Information Object Instance (SCI-IOI);
    incorporating information relating to said detected anatomical abnormalities into a DICOM Computer Aided Detection Structured Report Information Object Instance (CAD SR-IOI); and
    transferring said SCI-IOI and said CAD SR-IOI to a destination device.

17. The method of claim 16, said destination device being a viewing workstation, further comprising:
    extracting said second medical image from said SCI-IOI;
    receiving a third medical image at said viewing workstation, said third medical image being derived from said first medical image;

receiving said CAD SR-IOI at said viewing workstation;

displaying said second medical image and said third medical image on said viewing workstation; and rendering said CAD SR-IOI on said viewing workstation.

18. The method of claim 17, wherein said second medical image, said third medical image, and said rendering of said CAD SR-IOI are concurrently displayed on said viewing workstation.

19. The method of claim 17, said CAD SR-IOI including an equipment information entity identifier, further comprising setting said equipment information entity identifier to a substitute value not indicative of a manufacturer of a CAD system that performed said processing step.

20. The method of claim 17, said second medical image further comprising CAD annotations fixably integrated into pixels thereof, said CAD annotations including textual annotations.

21. The method of claim 20, wherein said first and third medical images are of diagnostic quality, and wherein said second medical image is of less-than-diagnostic quality.

22. The method of claim 16, wherein said destination device is selected from the group consisting of: a viewing workstation, an image archiving system, and a hardcopy printer.

23. The method of claim 16, wherein said transferring is performed over an electronic data communications network using the TCP/IP protocol.

24. The method of claim 16, wherein said transferring is performed using a tangible, portable storage medium selected from the group consisting of: a DVD, a CD, an optical storage medium other than a DVD or CD, a magnetic tape, and a portable flash memory device.

25. The method of claim 16, wherein said receiving said first medical image comprises receiving a Source Image Information Object Instance from a DICOM-conforming source device, the Source Image Information Object Instance comprising said first medical image.

26. The method of claim 16, wherein said step of receiving said first medical image comprises:

receiving a film-based image of said version of said anatomical part of the human body; and digitizing said film-based image to form said first medical image.

* * * * *